United States Patent [19]

Harandi et al.

[11] Patent Number: 4,814,519
[45] Date of Patent: Mar. 21, 1989

[54] PRODUCTION OF ETHERS FROM OLEFINS

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 139,517

[22] Filed: Dec. 30, 1987

[51] Int. Cl.$^4$ .............................................. C07C 41/06
[52] U.S. Cl. .................................... 568/697; 568/658; 568/579; 568/630; 585/664; 585/670; 585/671; 585/510; 585/530
[58] Field of Search ...................... 568/697, 658, 579; 585/664, 670, 671, 510, 530

[56] References Cited

U.S. PATENT DOCUMENTS

| 4,038,337 | 7/1977 | Manara et al. | 585/671 |
|---|---|---|---|
| 4,377,393 | 3/1983 | Schleppinghoff | 568/697 |
| 4,400,571 | 8/1983 | Robinson | 585/664 |
| 4,554,386 | 11/1985 | Groeneveld et al. | 568/697 |
| 4,581,474 | 4/1986 | Hutson et al. | 568/697 |
| 4,600,503 | 7/1986 | Angevine et al. | 208/251 H |
| 4,650,779 | 3/1987 | Goldstein | 502/38 |
| 4,714,787 | 12/1987 | Bell et al. | 568/697 |
| 4,731,490 | 3/1988 | Coughenour et al. | 568/697 |

FOREIGN PATENT DOCUMENTS 2071071  9/1981  United Kingdom .

OTHER PUBLICATIONS

U.S. appln. Ser. No. 687,414, filed 12/28/84.

Primary Examiner—Howard T. Mars
Attorney, Agent, or Firm—A. J. McKillop; C. J. Speciale; E. F. Kenehan, Jr.

[57] ABSTRACT

A process for the production of ethers from an olefin containing feedstock. The process includes two-stages for the production of ethers which comprises, in a first stage, isomerizing an olefin containing feedstock over a thermally stable layered metal oxide type catalyst having interspathic polymeric silica between the layers so as to produce iso-olefins and then, in a second stage, reacting the resultant iso-olefins with alcohols in the presence of an etherification catalyst so as to produce ethers from the iso-olegins.

13 Claims, No Drawings

PRODUCTION OF ETHERS FROM OLEFINS

The present invention relates generally to a process for the production of ethers from an olefin containing feedstock. More particularly, the subject invention relates to two-stage process for the production of ethers which includes, in a first stage, isomerizing an olefin containing feedstock over a thermally stable layered metal oxide type catalyst having interspathic polymeric silica between the layers so as to produce isoolefins and then, in a second stage, reacting the resultant isoolefins with alcohols in the presence of an etherification catalyst so as to produce ethers from the isoolefins.

Ethers, particularly alkyl ethers, are well known compounds which are used in a wide variety of applications such as solvents for organic synthesis, plasticizers, anaesthetics, fumigants and the like. In the petroleum industry, alkyl tert-alkyl ethers such as methyl t-butyl ether (often known simply as MTBE) and methyl tert-amyl ether (known as MTAE) are valuable compounds for improving the octane number when included in gasoline compositions. These ethers enable petroleum refiners to extend available supplies and obtain more usable fuel components from a given quantity of crude oil. Since ethers are composed simply of carbon, hydrogen and oxygen and contain no metals, their use as an octane rating enhancer for gasoline compositions avoids the environmental problems associated with the conventional gasoline additive agents such as tetraethyl lead. Furthermore, since many of the lower olefins derived from crude oil fractions are unsuitable for use in gasoline by themselves, conversion of these olefins to additive ethers adds to gasoline supplies.

Ethers can be prepared by a number of reaction routes from various starting materials as is well known in the art, e.g., the Williamson synthesis and the dehydration of alcohols. In petroleum refining operations where significant amounts of lower alkyl olefins are readily available from a steam cracking plant or a FCC unit, a commonly used synthesis route is the etherification reaction of these olefins with an alcohol in the presence of an acidic catalyst. The yield of valuable ethers is enhanced if the olefins subjected to etherification are iso-olefins, e.g., branched olefins containing a tertiary carbon.

In accordance with the process of the present invention, a lower olefin containing feedstock is catalytically reacted under specific conditions so as to isomerize and oligomerize the olefins contained therein a first stage so as to produce isoolefins and then the resultant isoolefins are, in a second stage, subjected to an etherification reaction with an alcohol in the presence of a suitable etherification catalyst. The catalyst used in the first stage is of the type, which under the specified conditions, promotes branching of the olefins during oligomerization such that the resultant product is highly iso-olefinic and especially suitable for etherification to yield product ethers of particular value.

The catalyst used in the first stage of the process of the invention for oligomerizing and isomerizing the olefin containing feedstock uses thermally stable layered metal oxides having interspathic polymeric oxides as the catalyst composition in isomerizing olefins. Prior to describing these catalytic compositions and methods for their manufacture, a brief background on layered materials may be beneficial.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bond generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the interlamellar spacing can be increased substantially by absorption of various swelling agents such as water, ethylene glycol, amines, ketones, etc., which enter the interlamellar space and push the layers apart. However, the interlamellar spaces of such layered materials tend to collapse when the molecules occupying the space are removed, for example, by exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness from the basal spacing.

The silicotitanate of the present invention has a substantially uniform interlayer distance sufficiently large to permit entry of ethylene molecules as well as to permit exit of higher hydrocarbons therefrom. Generally, the interlayer distance may range from about 1 to 30 or more angstroms, perferably about 6 to 20 angstroms.

The present invention may utilize a catalyst prepared from a layered titanate material which contains ion exchange sites having interspathic cations associated therewith. Such interspathic cations may include hydrogen ion, hydronium ion and akali metal cation. The starting material is treated with a "propping" agent comprising a source of organic cation such as organoammonium ion in order to effect an exchange of the interspathic cations resulting in the layers of the starting material being propped apart. The source of organic cations in those instances where the interspathic cations include hydrogen or hydronium ions may include a netural compound such as organic amine which is converted to a cationic analogue under such conditions. The organic cation should be capable of displacing or supplanting the original interspathic cations. The foregoing treatment results in the formation of a layered metal oxide of enhanced interlayer separation depending upon the size of the organic cation introduced.

After the ion exchange, the organic-"propped" species is treated with a compound capable of forming interspathic polymeric silica. Preferably, such compounds are capable of forming the polymeric silica upon hydrolysis. It is preferred that the organic cation deposited between the layers be capable of being removed from the layered oxide material without substantial disturbance or removal of the interspathic polymeric silica. For example, organic cations such as n-octylammonium may be removed by exposure to calcination or chemical oxidation conditions, preferably after the interspathic polymeric silica precursor has been converted to the polymeric silica.

The polymeric silica precursor-containing product is exposed to suitable conversion conditions, such as hydrolysis and/or calcination to form the layered material employed in the present invention. The hydrolysis step may be carried out by any method, for example, by interspathic water already present in organic "propped" layered oxide material. Because of the effect of interspathic water on hydrolysis, the extent of hydrolysis may be modified by varying the extent to which the organic-"propped" species is dried prior to addition of the polymeric silica precursor. As noted earlier, the product after conversion to the polymeric silica form may be exposed to conditions which remove the organic cation propping agents, e.g., exposure to elevated temperature.

The amount of interspathic polymeric silica contained within the final product can be greatly varied because the polymeric oxide precursor species are introduced in an electrically neutral form such that the amount of interspathic material incorporated within the layered titanate is not dependent upon the charge density of the original layered titanate. This allows the formation of materials with widely varying interlayer spacing, which permits accommodation of metal-containing molecules through the layered titanate.

The resulting product may have d-spacings greater than 10, 15, 20, 25 or even 30 angstroms. In particular, layered trititanates like $Na_2Ti_3O_7$ are useful starting materials. The starting materials generally comprise an interspathic cationic species between their layers. Trititanate is a commercially available material whose structure consists of infinite anionic sheets of titanium octahedra with intercalated alkali metal cations. The layered metal oxide component contains a stable polymeric oxide, preferably silica, between adjoining layers resulting in a heat-stable material which substantially retains its interlayer distance upon calcination. Silicotitanates exhibit the characteristic x-ray diffraction pattern of Table 1 below.

TABLE 1

| | Composite List of Principal X-Ray Powder* Diffraction Peaks for Silicotitanates | | |
|---|---|---|---|
| Line Number | 2 Theta Minimum | 2 Theta Maximum | $100/I/I_o$ (Relative Intensity) Range |
| 1 | less than or equal to 8.7 | | VS to W |
| 2 | 11.1–14.3 | | S to W |
| 3 | 11.8–15.2 | | M to W |
| 4 | 24.5–25.0 | | VS to W |
| 5 | 25.0–25.4 | | M to W |
| 6 | 28.5–30.2 | | VS to W |
| 7 | 29.8–30.6 | | S to W |
| 8 | 33.0–33.5 | | S to W |
| 9 | 43.2–43.5 | | M to W |
| 10 | 44.2–44.7 | | M to W |

TABLE 1-continued

| | Composite List of Principal X-Ray Powder* Diffraction Peaks for Silicotitanates | | |
|---|---|---|---|
| Line Number | 2 Theta Minimum | 2 Theta Maximum | $100/I/I_o$ (Relative Intensity) Range |
| 11 | 48.5–48.9 | | VS to M |
| 12 | 52.7–52.9 | | W |

*Theta minimum - 2 Theta maximum = Range of 2 theta-values observed for eight specific pillared silicotitanates These values were determined by standard techniques. The radiation was the K-alpha doublet of copper, and a scintillation counter spectrometer was used. The peak heights, I, and the positions as a function of 2 times theta, where theta is the Bragg angle, were determined. From these, relative intensities, $I/I_o$ where $I_o$ is the intensity of the strongest line or peak, and d is the interplanar spacing in angstroms (A), corresponding to the recorded lines, were calculated. The relative intensity in the table above is expressed as follows:

| Relative Intensity | 100 $I/I_o$ |
|---|---|
| VS (Very strong) | 60–100 |
| S (Strong) | 40–60 |
| M (Medium) | 20–40 |
| W (Weak) | 0–20 |

Variations in the interplanar spacing and relative intensity may occur as a result of ion exchange, changes in the composition of the silicotitanate, or exposure to calcination conditions.

The polymeric silica precursor employed may be an electrically neutral, hydrolyzable compound, such as tetrapropylorthosilicate, tetramethylorthosilicate, or preferably tetraethylorthosilicate.

The starting layered titanate is treated with an organic compound capable of forming cationic species such as organophosphonium or organoammonium ion, before adding the polymeric oxide source. Insertion of the organic cation between the adjoining layers serves to separate the layers in such a way as to make the layered titanate receptive to the interlayer addition of the electrically neutral, hydrolyzable, polymeric silica precursor. In particular, alkylammonium cations have been found useful in the present invention. $C_3$ and larger alkylammonium, e.g., n-octylammonium is readily incorporated within the interlayer species of the layered oxides, serving to prop open the layer in such a way as to admit the polymeric silica precursors. The extent of the interlayer spacing can be controlled by the size of the organoammonium ion employed. Indeed, the size and shape of the ammonium ion can affect whether or not the organoammonium ion can be interspathically incorporated within the layered oxide structure at all. For example, bulky cations such as tetrapropylammonium are not particularly suitable.

The organic ammonium cation precursor may be formed by combining a precursor amine and a suitable acid, e.g., mineral acids such as hydrochloric acid. The layered titanate starting material can then be combined with the resulting aqueous solution of ammonium ion to form a layered oxide containing intercalated organic material and water. The resulting "propped" product is then contacted with an electrically neutral, hydrolyzable polymeric silica precursor. After hydrolysis, preferably by exposure to interspathic water, the polymeric silica precursor forms a thermally stable polymeric silica. A final calcination step may be employed which is severe enough to remove the organic interspathic species. Remaining organic may also be removed, if desired, by a separate chemical treatment.

Layered titanate materials containing an exchangeable cation between the layers such as an alkali metal ion, e.g., sodium ion, may be treated by exchange with (1) ammonium ion, or (2) hydrogen ion, and/or (3) calcination to form a proton-exchanged with replacement cations such as cesium, cerium, cobalt, nickel, copper, zinc, manganese, platinum, lanthanum, aluminum, ammonium, hydronium and mixtures thereof. Ni(II) and Al(III) cations are of particularly significant interest as replacment cations. Layered titanates prepared without appreciable alkali metal content, e.g., by exchanging out the alkali metal with acid treatment, are also particularly well suited to such olefin isomerization. Such materials have an alkali metal content below about 1.0 weight percent, preferably below about 0.5 weight percent. The resulting product may contain anywhere from about 0.1 to 20 weight percent, preferably about 1 to 5 weight percent of element or elements and is formed into granules or extrudates for proper handling. Surface area may vary from about 10 to 500 m$^2$/g, preferably about 20 to 200 m$^2$/g.

An inorganic oxide binder may be added to the silicotitanate catalyst composition either before or preferably after incorporation of any proton exchanged material so that the resulting catalyst comprises about 1 to 99 weight percent, Preferably about 5 to 50 weight percent of inorganic oxide binder. Tabular alumina of the same particle size as the silicotitanate composition is particularly suited for compositing the silicotitanate. After compositing, the catalyst may have an overall surface area of about 1 to 400, preferably about 5 to 200 m$^2$/g.

In the first stage of the subject process, a feedstream containing olefins such as from a FCC unit is fed to a reactor containing a catalyst composition as described above and operating conditions are selected so as to maximize the production of C$_4$–C$_5$ iso-olefins, particularly tertiary isoolefins. This selection of conditions is made since the yield in the etherification of the second stage is higher when the resultant output isoolefin product stream contains much lower olefins than higher olefins. For example, the yield for the subsequent etherification stage is greater for C$_4$ olefins than C$_5$ olefins and, in a like manner, the yield is greater for C$_5$ olefins than C$_6$ olefins.

To achieve this end, the operating conditions for the first reaction stage are selected such that the reaction is conducted at a relatively high weight hour space velocity (WHSV) of about 1 to 80 hr$^{-1}$, a relatively moderate temperature of about 350° to about 750° F., and at a relatively low to moderate pressure of, for example, atmospheric up to about 200 psig. These operating conditions are different from those disclosed in copending U.S. patent application Ser. No. 897,787, filed June 27, 1986 which, in one aspect, relates to the oligimerization of C$_3$ and higher olefins using silicotitanate catalysts.

Within these limits the conditions of temperature and pressure may vary considerably depending upon equilibrium considerations, exact feed material, and presence or absence of diluents. Optimum conditions are those in which maximum yields of the desired iso-olefin products are obtained and hence considerations of temperature and pressure will vary within a range of conversion level designed to provide the highest selectivity and maximum yield. As was mentioned, higher operating temperatures and lower operating pressures seem to favor the formation of the desirable highly branched iso-olefins. For example, the minimum yield of iso-olefins in the first stage reaction is generally about 40 wt % based on a feed containing primarily propene and up to a majority (up to about 70% or more) of the iso-olefins are tertiary olefins.

The operating conditions employed for the first stage reaction may include carrying out the conversion of the feedstock in the vapor-phase by contact in a reaction zone, such as, for example, a fixed bed of catalyst composition, under conversion effective conditions. This process may be conducted in either batch or fluid bed operation with attendant benefits of either operation readily obtainable.

The resultant iso-olefin rich product stream is then, in a second stage, subjected to a catalytic etherification reaction to produce ethers. The feedstream may, in addition to the iso-olefins, may contain other hydrocarbons such as alkanes, aromatics, hydrogen and inert gases. The desired ethers formed in the second stage will have the formula R—O—R′ where R and R′ are alkyl groups of one to eight and three to six, respectively. The process is particularly adaptable in forming ethers where the sum of carbon atoms in R and R′ is from about four to ten, especially about six or less. Generally, such an etherification reaction is conducted in a reactor maintained at an elevated temperature and elevated pressure in the presence of a suitable etherification catalyst. Common catalysts for the etherification reaction are Lewis acids such as aluminum trichloride and boron trifluoride, mineral acids such as sulfuric acid, hydrochloric acid and phosphoric acid, organic acids such as alkyl and aryl sulfonic acids and ion exchange resins, particularly macroreticular resins. Also useful are the various porous crystalline silicate catalysts such as having the structure selected from the group consisting of ZSM-5, ZSM-11, ZSM-12, ZSM-23, zeolite Y, zeolite beta and the like. Reference is made to U.S. Pat. No. 3,702,886 which discloses ZSM-5, U.S. Pat. No. 3,709,979 which discloses ZSM-11, U.S. Pat. No. 3,832,449 which discloses ZSM-12, and U.S. Pat. No. 4,076,842 which discloses ZSM-23. Furthermore, U.S. Pat. No. 3,442,795 relates to a useful dealuminized zeolite Y suitable for etherification reactions. Another etherification catalyst is disclosed in U.S. Pat. No. 4,584,415 to Klotz and relates generally to a boron-containing silicate composition also described in U.S. Pat. Nos. 4,268,420 and 4,269,813. A preferred catalyst is a bi-functional ion exchange resin which is capable of etherifying and isomerizing the feed.

In the etherification reaction stage, one of the reactants is, of course, an alcohol, the selection of which is governed by the desired ether end product. or example, in an etherification process to produce methyl tertiary butyl ether (MTBE) or methyl tertiary amyl ether, methanol is reacted with isobutylene (2-methyl 1-butene) or isopentane (2-methyl 2-butane), respectively. The alcohol for the second stage may be an aliphatic, cycloalipathic or aromatic alcohol, which may be mono-, di- or polyhydric. An example of a suitable cycloaliphatic alcohol is cyclohexanol and an example of an aryl alcohol is phenol. Diols, such as ethylene glycol and propylene glycol and polyols, such as glycerol may be used. Mixtures of alcohols and/or diols may be employed if desired. Preferably, the alcohol reactant for the second stage of the process will be aliphatic and typical alcohols contain from one to about eight carbon atoms, preferably from one to about three carbon atoms. Suitable alcohols within the above description include methanol, ethanol, n-propanol, isopropanol, n-butanol, secbutanol, isobutyl alcohol, t-butyl alcohol, n-amyl alcohol, n-hexyl alcohol and n-octyl alcohol. Primary and secondary alcohols are preferred. The most preferred alcohol being methanol. Olefins most useful in this stage of the process contain two to about six carbon atoms and preferably about three to about five carbon atoms. Typical olefins include ethylene, propylene, 1-butene, 2-butene, isobutylene, 1-pentene, 2-pentene, 1-hexene, 2-hexene, 3-hexene, 3-methyl-pentene, 3-methyl-1-butene, 2-methyl-2-butene and 2-methyl-2-pentene.

In the second stage of the process of the invention, a feedstream of an olefin and an alcohol is contacted with a catalytic material. Generally, in a preferable portion of the process of this invention an olefin is contacted with the catalyst system in the liquid or vapor phase at a suitable reaction temperature, pressure and space velocity.

The particular operating conditions within an etherification reactor are dependent upon, among other things, the nature of the reactants and the desired conversion rate. Generally, suitable reaction conditions include a temperature of about 40° to about 200° C., a pressure of about 5 to about 50 atmospheres (500 to 5,000 kPa) at a weight hourly space velocity (WHSV) of about 0.1 to about 24 $hr^{-1}$. In a typical process scheme, an alcohol and olefin containing feedstream is contacted with such catalyst in a reactor at about 50° to about 150° C. at a pressure of about 6 to about 25 atmospheres (600 to 2,500 kPa) at a WHSV of about 0.5 to about 12$hr^{-1}$. Preferably the ether formation portion of the process of this invention is conducted at about 60° to about 140° C. at a pressure of about 15 to about 20 atmospheres (150-2,000 kPa) at a WHSV of about 1.0 to about 10$hr^{-1}$. As was mentioned, the second stage of the process may be carried out in the liquid phase or in the vapor phase, preferably in the liquid phase. Reaction conditions which result in the formation of an ether will depend on whether the process is carried out in the liquid or the vapor phase and to some extent on the nature of the reactants. In the liquid phase the pressure is suitably that pressure which maintains a liquid phase at the reaction temperature. Solvents may be employed if so desired. Suitable solvents include hydrocarbons, e.g., alkanes such as hexane and octane. The process may be carried out batchwise or continuously, preferably continuously. The resultant ethers may be then subjected to a separation from the product stream such as for example, by distillation. The amount of iso-olefin fed to the second stage of the process may be greater or less than the stoichiometric amount required to completely react with the alcohol.

Additional details as to specific etherification reactions parameters and ether product separation from unreacted feed may be found in U.S. Pat. No. 4,605,787 to Chu et al. incorporated herein by reference, as well as in the discussion presented in U.S. Pat. No. 4,575,566 and the patents mentioned therein, all of which are incorporated by reference.

The following examples are cited to illustrate more specifically the preparation and use of the catalysts for this invention, but are not to be construed as limiting in scope.

EXAMPLE 1

Preparaion of $H_2Ti_3O_7$

Acid titanate, $H_2Ti_3O_7$, was prepared from exchange of Na in $Na_2Ti_3O_7$ with 1 M HCl in triplicate as described: 780.7 g 37.4% HCl was diluted to 8 liters total volume with water in a 12 liter 4-necked round bottom flask equipped with a mechanical stirrer, reflux condenser, and thermometer. 500 grams of $Na_2Ti_3O_7$ were added, and the resulting mixture was heated with stirring at 75°-80° C. for 24 hours. The solution was then filtered and washed with 2 liters of hot water. The procedure was repeated in triplicate. After the third exchange, the product was washed with hot water until chloride free. The product after drying in vacuo at 77° C. had an X-ray diffraction pattern similar to that reported for $H_2Ti_3O_7$ and the following composition (wt %):

| | |
|---|---|
| $TiO_2$ | 93.4 |
| Na | 0.28 |

EXAMPLE 2

One kg of $Na_2Ti_3O_7$ was exchanged in triplicate with 16 liters of 1.0 M HCl with stirring at 170° C. for 24 hours. The solid was filtered and washed with 4 liters of water after the first two exchanges. After the third exchange, the product was filtered, washed chloride-free with water and dried at 77° C. for one hour in vacuo. A mixture of 700 g of this material in 700 g of octylamine and 10.5 liters of water was refluxed with stirring for 23 hours. The product was filtered, washed with 10 liters of hot water, and dried at room temperature for 3 days. 600 g of this product were stirred in 4 kg of tetraethylorthosilicate for 67 hours at room temperature, filtered, and then dried for 24 hours at room temperature, 800 g of the dried product were calcined in $N_2$ at 510° C. for 2 hours and in air for one hout at 510° C. The final silicotitanate product had a surface area of 394 $m^2/g$ and the following composition (wt %):

| | |
|---|---|
| $TiO_2$ | 65.2 |
| $SiO_2$ | 37.3 |
| Na | 0.34 |
| Ash | 97.61 |

A mixture of 900 g $Na_2Ti_3O_7$, 770 g n-octylamine, 559 g 37.8% HCl and 5 liters of water was refluxed for 22 hours. The solution was cooled to 70° C. and 281 g of 37.8% HCl were added. The product was filtered, washed with 10 liters of hot water, and dried 20 hours at room temperature. The solid product was stirred in 3 liters of absolute ethanol at room temperature for one hour, filtered, and air-dried at room temperature for 24 hours. This material was then stirred in 4 liters of water at room temperature for 23 hours, filtered, and dried for 24 hours at room temperature. 825 g of the dried product were mechanically stirred in 5.5 g of tetraethylorthosilicate in a 10 liter beaker covered with perforated aluminum foil for 68 hours at room temperature and then filtered and dried in air at room temperature for about 4 days. This material was calcined in nitrogen at 510° C. for 2 hours and then in air for one hour at 510° C. The silicotitanate product had a surface area of 200 $m^2/g$ and the following composition (wt %):

| | |
|---|---|
| TiO$_2$ | 70.2 |
| SiO$_2$ | 21.7 |
| Na | 3.3 |
| Ash | 100.0 |

EXAMPLE 4

Overhead from a FCC unit is fed to a stirred tank reactor maintained at about 500° F. and 100 psig which contains the catalytic composition of Example 3. The overhead has the following composition:

| Component | Mol % |
|---|---|
| H$_2$ | 21.6 |
| Inerts | 15.7 |
| H$_2$S | 3.4 |
| C$_1$ | 23.0 |
| C$_2$= | 11.3 |
| C$_2$ | 12.7 |
| C$_3$= | 5.2 |
| C$_3$ | 1.6 |
| iC$_4$ | 1.0 |
| C$_4$= | 1.8 |
| nC$_4$ | 0.3 |
| C$_5$+ | 2.4 |

The resultant iso-olefin rich product stream is then introduced into a catalytic etherification reactor in the presence of a zeolite beta silicate catalyst and an ethanol rich alcohol co-fed stream. The liquid phase reactor is maintained at about 100° C. and a pressure of about 20 atmospheres. The resultant ether rich stream from this reactor are then subjected to distillation for separation into the various ether components.

While there has been shown and described what is considered to be preferred embodiments of the present invention, it will be obvious to those skilled in the art that various changes and modifications may be made therein without departing from the invention as defined in the appended claims.

It is claimed:

1. A process for producing ethers from lower olefins, the process comprising, in a first stag, contacting a reaction mixture comprising olefins under reaction conditions of elevated temperature and pressure with a catalyst to produce an isoolefin product stream, the catalyst comprising a layered titanate composition which contains interspathic polymeric silica, the reaction conditions comprising a temperature of about 350° to 750° F., a moderate pressure of about 0 to 200 psig, and a WHSV of up to about 80, and then, in a second stage, contacting the iso-olefins from the first stage with an alcohol and an etherification catalyst under reaction conditions including an elevated temperature.

2. The process of claim 1, wherein said second stage reaction conditions comprise a temperature of 40° to 200° C., a pressure bf about 5 to about 50 atmospheres, and a WHSV of about 0.1 to 24.

3. The process of claim 1, wherein said layered titanate composition is prepared by swelling a layered trititanate with an alkylamine, contacting the swelled trititanate with a tetraalkylorthosilicate to introduce oxides of silicon between the layers of said trititanate, and exposing the resulting trititanate to hydrolysis conditions.

4. The process of claim 3, wherein said layered trititanate is Na$_2$Ti$_3$O$_7$, said alkylamine is n-octylamine, and said tetraalkylorthosilicate is tetraethylorthosilicate.

5. The process of claim 4, wherein said layered trititanate is hydrogen-exchanged prior to said swelling.

6. The process of claim 5, wherein said layered trititanate is hydrogen-exchanged prior to said swelling.

7. The process of claim 1, wherein the olefin of the reaction mixture includes at least one of C$_2$ to C$_6$ olefins.

8. The process of claim 1, wherein the olefin of the reaction mixture includes at least one of C$_4$ and C$_5$ olefins.

9. The process of claim 1, wherein said catalyst comprises about 0.1 to 90 weight percent of an inorganic binder.

10. The process of claim 1, wherein the catalyst for the second stage etherification catalyst includes a porous crystalline silicate catalyst.

11. The process of claim 10, wherein the catalyst for the second stage includes a porous crystalline aluminosilicate.

12. The process of claim 11, wherein the zeolite is zeolite beta.

13. The process of claim 1, wherein said layered titanate composition is prepared from a silicotitanate having the x-ray diffraction pattern set forth in the following Table:

| Line Number | 2 Theta Minimum | 2 Theta Maximum | 100/I/I$_o$ (Relative Intensity) Range |
|---|---|---|---|
| 1 | less than or equal to 8.7 | | VS to W |
| 2 | 11.1–14.3 | | S to W |
| 3 | 11.8–15.2 | | M to W |
| 4 | 24.5–25.0 | | VS to W |
| 5 | 25.0–25.4 | | M to W |
| 6 | 28.5–30.2 | | VS to W |
| 7 | 29.8–30.6 | | S to W |
| 8 | 33.0–33.5 | | S to W |
| 9 | 43.2–43.5 | | M to W |
| 10 | 44.2–44.7 | | M to W |
| 11 | 48.5–48.9 | | VS to M |
| 12 | 52.7–52.9 | | W |

* * * * *

UNITED STATES PATENT AND TRADEMARK OFFICE
CERTIFICATE OF CORRECTION

PATENT NO. : 4,814,519

DATED : March 21, 1989

INVENTOR(S) : Mohsen N. Harandi and Hartley Owen

It is certified that error appears in the above-identified patent and that said Letters Patent is hereby corrected as shown below:

Title page, Abstract line 10, "iso-olegins" should be --iso-olefins--.

Col. 1, line 8, "isomerizing" should be -- reacting --.

Col. 5, line 30, "Preferably" should be --preferably--.

Col. 5, line 53, "80 hr$^{311}$" should be --80 hr$^{-1}$--.

Col. 6, line 55, ".or" should be --.For--.

Col. 7, line 30, "24$^{31}$" should be --24 hr$^{-1}$--.

Col. 7, line 39, "10 hr$^{311}$" should be --10 hr$^{-1}$--.

Col. 8, line 3, "Preparaion" should be --Preparation--.

Col. 9 cl 1, line 46, "stag" should be --stage--.

Col. 10, cl 5, line 1, "4" should be --3--.

Col. 10, cl 6, "5" should be --4--.

Signed and Sealed this

Twelfth Day of December, 1989

Attest:

JEFFREY M. SAMUELS

Attesting Officer    Acting Commissioner of Patents and Trademarks